United States Patent
Sanders et al.

(10) Patent No.: US 10,292,671 B2
(45) Date of Patent: May 21, 2019

(54) DATA-DRIVEN SURROGATE RESPIRATORY SIGNAL GENERATION FOR MEDICAL IMAGING

(71) Applicant: Siemens Medical Solutions USA, Inc., Malvern, PA (US)

(72) Inventors: James C. Sanders, Nürnberg (DE); Alexander Hans Vija, Evanston, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 15/567,492

(22) PCT Filed: Apr. 25, 2016

(86) PCT No.: PCT/IB2016/052322
§ 371 (c)(1),
(2) Date: Oct. 18, 2017

(87) PCT Pub. No.: WO2016/178115
PCT Pub. Date: Nov. 10, 2016

(65) Prior Publication Data
US 2018/0289349 A1    Oct. 11, 2018

Related U.S. Application Data

(60) Provisional application No. 62/156,470, filed on May 4, 2015.

(51) Int. Cl.
*G06K 9/00* (2006.01)
*A61B 6/00* (2006.01)
(Continued)

(52) U.S. Cl.
CPC ............ *A61B 6/5217* (2013.01); *A61B 6/037* (2013.01); *A61B 6/486* (2013.01); *A61B 6/5264* (2013.01);
(Continued)

(58) Field of Classification Search
None
See application file for complete search history.

(56) References Cited

U.S. PATENT DOCUMENTS

2012/0281897 A1    11/2012  Razifar et al.

OTHER PUBLICATIONS

International Search Report for corresponding application No. PCT/IB2016/052322 dated Jul. 7, 2016.
(Continued)

*Primary Examiner* — Atiba O Fitzpatrick

(57) ABSTRACT

Projection data are acquired by one or more gamma detectors of a medical imaging system. The counts for each projection are binned into time bins to provide respective frames. Using a computer processor, a respective weight factor is computed for each pair of input points among a plurality of input points associated with respective time bins, each input point being an M-dimensional representation of the frame corresponding to the associated time bin for one of the projections. Each weight factor is inversely proportional to a distance computed between the corresponding pair of input points according to an adaptive distance measure that is dependent on the projection data corresponding to said one projection. An N-dimensional surrogate respiratory signal (N<M) is generated based on an optimization of a nonlinear objective function using the weight factors, wherein the surrogate respiratory signal is indicative of patient respiratory activity.

20 Claims, 9 Drawing Sheets

(51) Int. Cl.
*A61B 6/03* (2006.01)
*G06T 7/20* (2017.01)

(52) U.S. Cl.
CPC .............. *A61B 6/5288* (2013.01); *G06T 7/20* (2013.01); *A61B 6/4266* (2013.01); *G06T 2207/10104* (2013.01); *G06T 2207/10108* (2013.01)

(56) References Cited

OTHER PUBLICATIONS

Fuerst Sebastian et al: "Motion Corection Strategies for Integrated PET/MR"; The Journal of Nuclear Medicine; vol. 45 No. 2; pp: 261-269; XP055283891; ISSN: 0161-5505; DOI:10.2967/jnumed. 114.146787 / Jan. 8, 2015.
Van Der Maaten Laurens et al: "Dimensionality Reduction: A Comparative Review"; Tilburg University Technical Report; vol. TiCC TR 2009-005; NL; pp. 1-36; XP008132365; / Oct. 26, 2009.
Thielemans Kris et al: "Comparison of Different Methods for Data-driven Respiratory Gating of PET Data"; 2013 IEEE Nuclear Science Symposium and Medical Imaging Conference; pp. 1-4; XP032601818; DOI: 10.1109/NSSMIC.2013.6829055 / Oct. 27, 2013.
Wachinger Christian et al: "Manifold learning for image-based breathing gating in ultrasound and MRI"; Medical Image Analysis 16.4; pp. 806-818, XP055283896; ISSN: 1361-8415; DOI:10.1016/j.media.2011.11.008 / Aug. 12, 2011.

DATA-DRIVEN SURROGATE RESPIRATORY SIGNAL GENERATION FOR MEDICAL IMAGING

CROSS-REFERENCE TO RELATED APPLICATIONS

This application claims priority under 35 U.S.C. § 119(e) from U.S. Provisional Application Ser. No. 62/156,470 filed May 4, 2015, the entirety of which is hereby incorporated by reference herein.

FIELD

The present disclosure generally relates to signal processing that supports improved medical imaging. In particular, the present disclosure relates to data-driven techniques for generating a surrogate respiratory signal based on projection data alone, instead of using an additional dedicated device to obtain the respiratory signal.

BACKGROUND

In the medical context, imaging of patients plays an important role in numerous scenarios. In one type of nuclear medical imaging known as Single Photon Emission Computed Tomography (SPECT), the primary imaging task is to accurately determine and depict the spatial 3D or 4D distribution of a radioactive isotope (radioisotope) used as a tracer (radiotracer) in the imaged object. A tomographic gamma camera is used to acquire multiple projections from sufficiently many different viewing angles in data space (e.g., 2D space), and a computer performs tomographic image reconstruction to generate an image in a higher-dimensional (e.g., 3D or 4D) image space. For example, a gamma photon-emitting radioisotope may be introduced into a patient's body, and any of various techniques can be used to bind the radioisotope to a location of interest in the body. Typically, one or more gamma cameras are attached to a gantry of the imaging system, and the gantry rotates and/or shifts, causing the gamma camera(s) to rotate and/or shift relative to the patient who is positioned on a bed. Detectors of the gamma camera(s) acquire projection data at each orientation by detecting gamma photons emitted by the radioisotope, resulting in a projection data set. Using the techniques of tomographic reconstruction, an image is generated based on the projection data set.

Because the duration of the acquisition of a projection view (dwell time) for each projection in a SPECT acquisition is typically at least as long as the period of a typical human respiratory cycle, it is impossible to require a patient to hold his/her breath during the acquisition of all projections needed for SPECT imaging to avoid any artifacts from respiratory motion. Typically, the patient continues to breathe during the acquisition, and because the dwell time or exposure is at least as long as the respiratory cycle, blurring of the projection view occurs. This blurring is a known problem in, e.g. cardiac SPECT imaging, where because of the volume change of the lungs the diaphragm impinges and moves the heart itself. Other examples are motion of tumors in lungs and the liver.

To address the problem of blurring caused by cycle motion, one uses the well known technique of gating, whereby one subdivides an acquisition into multiple (e.g. G=8) time bins (also known as time gates) during each of which there is relatively little motion of body parts. Each projection view now results in G gated projections corresponding to the individual gates, and proper booking now generates a total of G projection data sets that can be reconstructed into G reconstructed volumes, or images each depicting a different motion state. One can then evaluate the images separately. In order to perform the gating process, a physiological trigger is used. In general, if the cyclical motion is measured one can extract, e.g., trigger and amplitude. A common approach for obtaining such a signal has been to use an external sensor such as a pressure sensor, spirometer, piezoelectric belt, or camera to obtain information regarding respiratory state. There are several problems associated with the use of an external sensor for tracking respiratory state. In most cases the measurement is not a direct measurement of the internal organ, but rather the consequence of the internal motion, such as pressure change or visual chest movement. In addition, such a sensor represents extra hardware that must be installed, calibrated, and synchronized with the imaging system. A sensor affixed to a patient may be uncomfortable, particularly if it is bulky. Additionally, the presence of one or more detectors near the patient imposes space constraints and may render large external sensors impractical.

Some work has previously been pursued on approaches for generating a surrogate respiratory signal that are data driven, i.e., based on the projection data itself, without the need for an external sensor. But, known data-driven approaches do not work well with traditional SPECT. For example, some prior data-driven approaches have been based on tracking count rate variations and image centroids in the PET context. But, traditional SPECT is not tomographically consistent over time, as acquisitions involve sequential planar projections, and only at the end of the last view can a tomograph can be formed. PET, on the other hand, uses a ring detector, allowing tomographic data to be acquired simultaneously from all view angles at each time point. In the latter case, motion is always seen as blur, while in traditional SPECT, different blurring may have been measured at different viewing angles, resulting not only in a final image that is blurred, but one that may contain more severe artifacts, such as shape distortions or "bumpiness." Regardless of whether PET or SPECT image formation is used, emission tomography data is always noisy because of insufficient counting statistics resulting from the desire to limit the dose burden to the patient, and reasonably short acquisition times to allow for an efficient clinical workflow. In such imaging scenarios lacking temporal tomographic consistency and involving noisy data, any data driven method must be robust with respect to noise and flexible enough to accommodate different motion patterns encountered from different view angles.

SUMMARY

In some embodiments of the present disclosure, a method of signal processing for medical imaging includes providing projection data acquired by one or more gamma detectors of a medical imaging system. The projection data represent detected counts of photons emitted by a radioisotope within a patient, where the counts are detected for a plurality of projections. The counts for each projection are binned into a plurality of time bins to provide respective frames of the projection data. Using a computer processor of the medical imaging system, a respective weight factor is computed for each pair of input points among a plurality of input points associated with respective time bins, each input point being an M-dimensional representation of the frame corresponding to the associated time bin for one of the projections, wherein each weight factor is inversely proportional to a distance computed between the corresponding pair of input points according to an adaptive distance measure that is dependent on the projection data corresponding to said one projection. Using the computer processor, an N-dimensional surrogate respiratory signal is generated based on an optimization of a nonlinear objective function using the weight factors, wherein N<M and the surrogate respiratory signal is indicative of respiratory activity by the patient.

In some embodiments of the present disclosure, a method of signal processing for medical imaging includes providing projection data acquired by one or more gamma detectors of a medical imaging system. The projection data represent detected counts of photons emitted by a radioisotope within a patient, where the counts are detected for a plurality of projections. The counts for each projection are binned into a plurality of time bins to provide respective frames of the projection data. Using a computer processor of the medical imaging system, a local neighborhood is computed for each input point of a plurality of input points associated with respective time bins, each input point being an M-dimensional representation of the frame corresponding to the associated time bin for one of the projections, wherein each local neighborhood is adaptively computed based on the plurality of input points. Using the computer processor, within the local neighborhood of at least one of the input points, a distance is computed between said at least one input point and each other input point in the local neighborhood according to a distance measure that is dependent on the projection data corresponding to said one projection. Using the computer processor, an N-dimensional surrogate respiratory signal is generated based on an optimization of a nonlinear objective function using the computed distances, wherein N<M and the surrogate respiratory signal is indicative of respiratory activity by the patient.

In some embodiments, a method for medical imaging includes detecting, at one or more gamma detectors of a medical imaging system, counts of photons emitted by a radioisotope within a patient. The counts are detected for a plurality of projections corresponding to respective orientations of the one or more gamma detectors relative to the patient. The counts for each projection are binned into a plurality of time bins to provide respective frames of the projection data. Using a computer processor of the medical imaging system, each frame for one of the projections is vectorized to produce a plurality of input points. Each input point is an M-dimensional vector representation of the corresponding frame. Using said computer processor, an adjacency matrix is computed based on the plurality of input points. Each value in the adjacency matrix represents a distance between a pair of said input points according to an adaptive distance measure based on a factor dependent on said one projection. Using said computer processor, one or more eigenvectors of a Laplacian matrix based on the adjacency matrix are computed. Using said computer processor, an N-dimensional surrogate respiratory signal is generated based on the one or more eigenvectors, wherein the surrogate respiratory signal is indicative of respiratory activity by the patient and N<M. Using said computer processor, a plurality of time gates are determined based on the surrogate respiratory signal. Using said computer processor, an image of a portion of the body of the patient is reconstructed based on the projection data and the plurality of time gates.

In some embodiments, a machine-readable storage medium tangibly embodies a program of instructions executable by a computer processor of a medical imaging system to cause the computer processor to perform operations described above regarding the foregoing methods of signal processing for medical imaging.

In some embodiments, a medical imaging system includes one or more gamma detectors, a computer processor, and a computer readable storage medium. The storage medium tangibly embodies a program of instructions executable by the computer processor to cause the computer processor to perform operations described above regarding the foregoing methods of signal processing for medical imaging.

BRIEF DESCRIPTION OF THE DRAWINGS

The following will be apparent from elements of the figures, which are provided for illustrative purposes and are not necessarily to scale.

DETAILED DESCRIPTION

Figure 1:
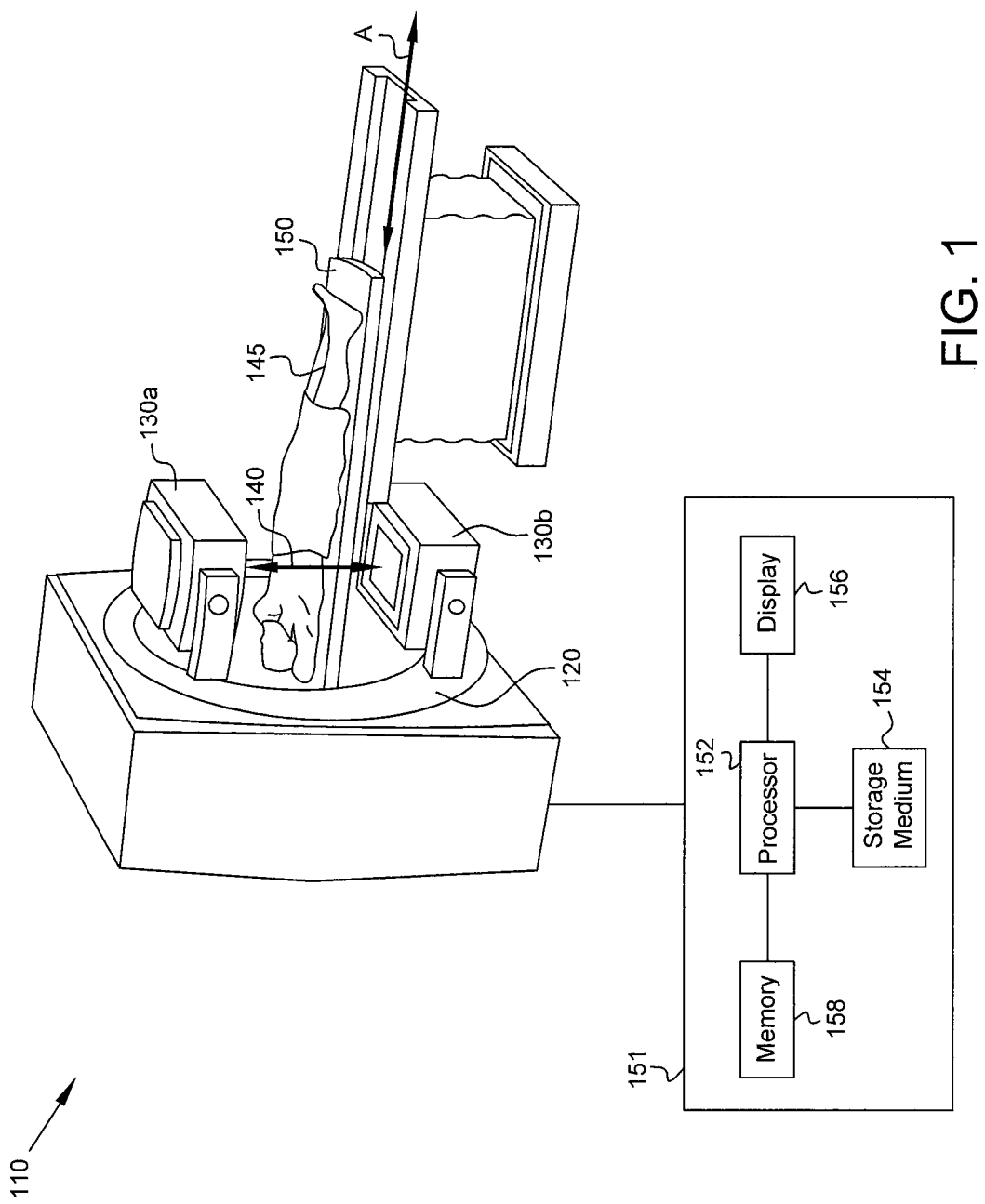
FIG. 1 is a diagram of a medical imaging system in accordance with some embodiments of the present disclosure.

This description of the exemplary embodiments is intended to be read in connection with the accompanying drawings, which are to be considered part of the entire written description.

Various embodiments of the present disclosure provide a surrogate respiratory signal using data-driven techniques in a fully automated manner so that artifacts associated with respiratory motion can be reduced or eliminated in SPECT imaging. Dimensionality reduction (DR) is used to generate a surrogate signal that is of lower dimensionality than input points arising from projection data. Some efforts have previously been made regarding application of principal component analysis (PCA)—a linear, global DR method—to surrogate signal estimation with PET data. PET systems are different from SPECT systems in two primary ways. The first of these is the fact that PET data is acquired from all angles about the patient simultaneously. When performing respiratory surrogate estimation using DR, this complete tomographic coverage provides much redundancy in the projection space that insulates against non-idealities arising from, for example, attenuation and foreshortening that may arise at individual view angles. In SPECT, where an acquisition comprises sequential projections from disjoint views, this redundancy is lacking, as the DR method must operate on individual views separately. Respiratory motion may manifest itself in the projection space in complex motion patterns that differ radically from view to view. For this reason, linear DR methods such as PCA that make explicit assumptions about the nature of the necessary mapping from the high- to the low-dimensional space may be too constrained to accurately extract a surrogate signal in all cases. Therefore, in various embodiments nonlinear DR methods are used for determining arbitrary mappings, resulting in performance benefits.

The second way in which linear, global DR approaches for surrogate signal estimation fail in the case of SPECT relates to noise. PET systems have a much higher sensitivity than conventional SPECT systems, which leads to less-noisy projection data. PCA is a global DR method based on an analysis of the data's covariance matrix, which includes all of the input data in its computation. By incorporating all of the input data to estimate each of the output points, PCA becomes less robust to outliers and allows data points perturbed by noise to skew the DR mapping for all other points in the data. In contrast, local DR methods use a kernel or a local neighborhood to only consider input data points that are close to each other according to some distance measure when determining the mapping for a particular output point. This locality makes local DR methods more robust to noise and outliers than global DR methods, e.g., if the desired output signal is continuous and of low-dimension compared to the size of the neighborhood.

To address the foregoing deficiencies of linear, global DR approaches, in various embodiments a nonlinear, local DR approach is used. Examples of nonlinear, local DR approaches that may be used include: Laplacian eigenmaps, diffusion maps, isomap, and local linear embedding. For convenience, an implementation using Laplacian eigenmaps is described in examples below, but other nonlinear, local DR techniques may be used as well. In various embodiments, acquired projection data are processed automatically by a computer processor, with no manual intervention or tuning required, to generate the surrogate respiratory signal. Unlike the traditional techniques that involve tuning of one or more scale parameters to an acceptable constant value a priori, which can be a laborious and/or inaccurate process, embodiments of the present disclosure set the scale parameter(s) adaptively so that performance under a wide range of conditions is enabled without such a priori tuning of the scale parameter.

FIG. 1 is a diagram of a medical imaging system 110 in accordance with some embodiments of the present disclosure. Medical imaging system 110 includes detectors 130a, 130b (collectively, detectors 130) of gamma cameras connected to gantry 120. In the example of FIG. 1, a SPECT imaging system including a pair of detectors 130a, 130b is shown, but a different number of detectors (one or more) may be used in various embodiments, and the imaging modality may be PET instead of SPECT. Gantry 120 is capable of rotating and/or shifting relative to patient 145 lying on bed 150. Bed 150 is slidable along axis A to enable imaging of any body part of patient 145. At each orientation (corresponding to respective camera stops) of detectors 130, gamma photons 140 emitted by a radioisotope within patient 145 as part of a nuclear decay process are detected by the detectors.

Each such camera stop corresponds to a single projection for which projection data are acquired, and projection data for multiple projections are acquired during the full acquisition, which may take several minutes. The projection data may be stored in memory, e.g., memory 158 of computer 151 coupled to detectors 130. A processor 152 of computer 151 of medical imaging system 110 processes the projection data, e.g., according to instructions stored on (tangibly embodied on) a non-transitory computer-readable (machine-readable) storage medium 154, to reconstruct one or more images (e.g., 3D or 4D image(s)) of a portion of the patient's body. The images may be displayed on a display 156 that is viewable by a clinician or other person. In some embodiments, one computer is used for acquisition and another computer is used for subsequent processing (e.g., to generate a surrogate respiratory signal and reconstruct an image), and in other embodiments, a single computer may be used for acquisition and processing. For convenience, computer 151 is shown in FIG. 1, and one of ordinary skill in the art recognizes that computing tasks may be performed by one computer or split among multiple computers.

Figure 2:
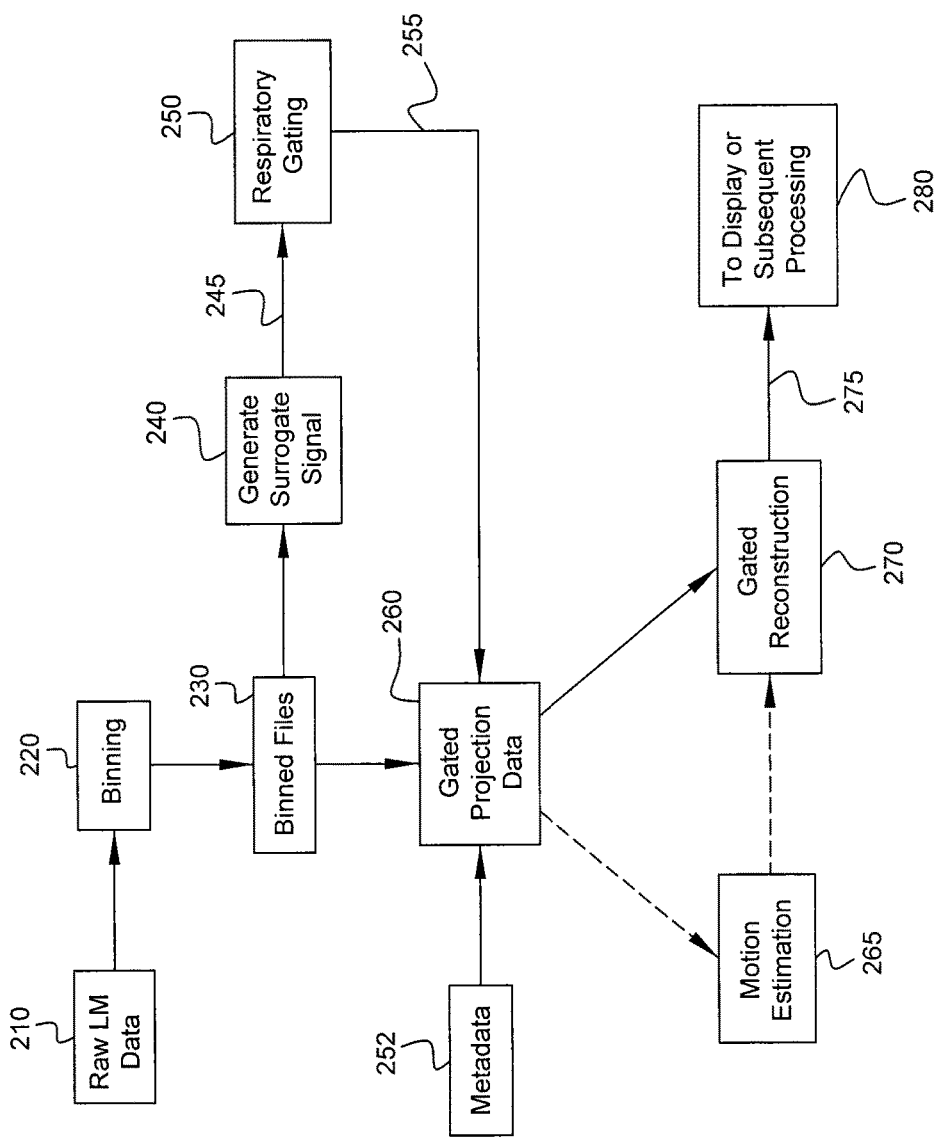
FIG. 2 is a flow diagram of processing performed by a computer in accordance with some embodiments.

Example processing performed by computer 152 is shown in more detail in FIG. 2. The processing shown in FIG. 2 corresponds to one implementation only, and other implementations can be used. Incoming list-mode data 210 representing detected photon counts may be retrieved from memory 158 and binned (block 220) temporally and spatially. The list-mode data 210 are binned temporally into time bins to provide respective frames of the projection data. Each frame may correspond to a duration of, for example, 200 or 300 ms in some implementations, although different durations may be used. The detected photons are then spatially binned into pixel matrices (e.g., 256×256 pixel matrices with 2.4 mm isotropic pixels). After binning, the frames may optionally be smoothed spatially (e.g., with a 32×32 pixel moving average window) and/or temporally (e.g., with a two-time-bin moving average window). The binned data may be written to one or more files 230 for further processing. Various parameters regarding spatial and temporal binning may be changed to suit the needs of a particular implementation.

In some embodiments, to ensure that the narrow time bins have sufficient data to enable generation of a surrogate respiratory signal, all detected counts are used, regardless of energy. The resulting projections may have low contrast, but even if they are not usable for image reconstruction, they may be useful for motion estimation.

A surrogate respiratory signal 245 is generated (block 240) based on the binned projection data. In the dual-headed SPECT example of FIG. 1, projections from two detectors 130a, 130b are acquired simultaneously at each camera stop, and frames from both detectors are concatenated together. Therefore, using the numbers from the foregoing implementation example, the projection data includes, for each camera stop, a plurality of frames (the number of frames may be denoted T) with each frame being a matrix having 256 rows and 512 columns (512=2*256). Alternatively, each frame may have 512 rows and 256 columns. One of ordinary skill recognizes that the frames may be stored in various representations, and the foregoing frame details are presented merely as an example.

In one example implementation, each frame is vectorized to produce a vector that has many rows and one column, or one row and many columns. For example, because $2^8=256$ and $2^9=512$, each frame may vectorized to produce a K-tuple where $K=2^{8+9}=2^{17}$. In other words, each frame may be considered as an ordered list of K real numbers, or equivalently, a point in K-dimensional space (in mathematical notation, a point in $R^K$ where R represents the field of real numbers). By considering all T frames, the vectorized projection data may be considered as columns in a matrix with K rows and T columns. One of ordinary skill in the art recognizes that vectorization may be performed in various ways, e.g., by considering elements in one row first and proceeding to the next column, or vice versa.

In one example implementation, the dimensionality reduction technique referred to as Laplacian eigenmaps (LE) is used for generating (block 240; described in more detail below) a surrogate respiratory signal 245 with dimensionality much lower than the above-described vectorized projection data. The basic goal of LE is to search for a nonlinear embedding in a high-dimensional space by minimizing an objective function. This minimization may be accomplished by performing an eigenvalue decomposition, with a resulting eigenvector providing the lower-dimensional output of the LE processing. Unlike linear dimensionality reduction techniques such as principle component analysis (PCA), LE is a more robust, nonlinear statistical analysis technique. Although nonlinear variants of PCA exist, they are based on assumed motion models that may be inapplicable to actual data. In contrast, the nonlinear dimensionality reduction approach in embodiments of the present disclosure avoids assumptions about motion models and is thus more broadly applicable.

For convenience, the input data to the LE processing (the vectorized projection data) may be called input points $x_i$ (or simply x for convenience, with the indexing by time bins being understood) in M-dimensional space, where i is an index for the time bins or frames. LE processing can be used to generate a surrogate respiratory signal that varies over time, with each value of the surrogate respiratory signal being an N-tuple, with N much less than M (N<<M). For example, N may equal 1, so that each value of the surrogate respiratory signal is a real number (a 1-dimensional quantity) and the values can be interpreted as amplitudes. Specifically, the goal of LE processing is to compute a matrix $Y=[y_i, \ldots, y_T]$ that minimizes the following objective function:

$$\sum_{i,j} \|(y_{*,i} - y_{*,j})\|_2^2 w_{i,j}, \quad (1)$$

where the subscripts "*,i" and "*,j" denote column vectors of Y corresponding to N-dimensional output points at time bins (or frames) i and j, respectively. Determining respective values for output points y that minimize equation (1) ensures that input points that are close to one another in the high dimensional (e.g., M-dimensional) space mapped (by Laplacian eigenmapping) to output points that remain close in the low dimensional (e.g., N-dimensional) space as well.

Respiratory gating (block 250) is performed based on surrogate respiratory signal 245. The resulting gating signal 255 and metadata 252 are used to generate gated projection data 260, which may be used for gated image reconstruction 270. In some embodiments, the gated projections serve as an intermediate output to be processed by a subsequent optional respiratory motion estimation module 265. The reconstructed images 275 may be displayed (e.g., on display 156) or further processed, e.g., by classification or diagnosis routines, as shown by block 280.

Figure 3:
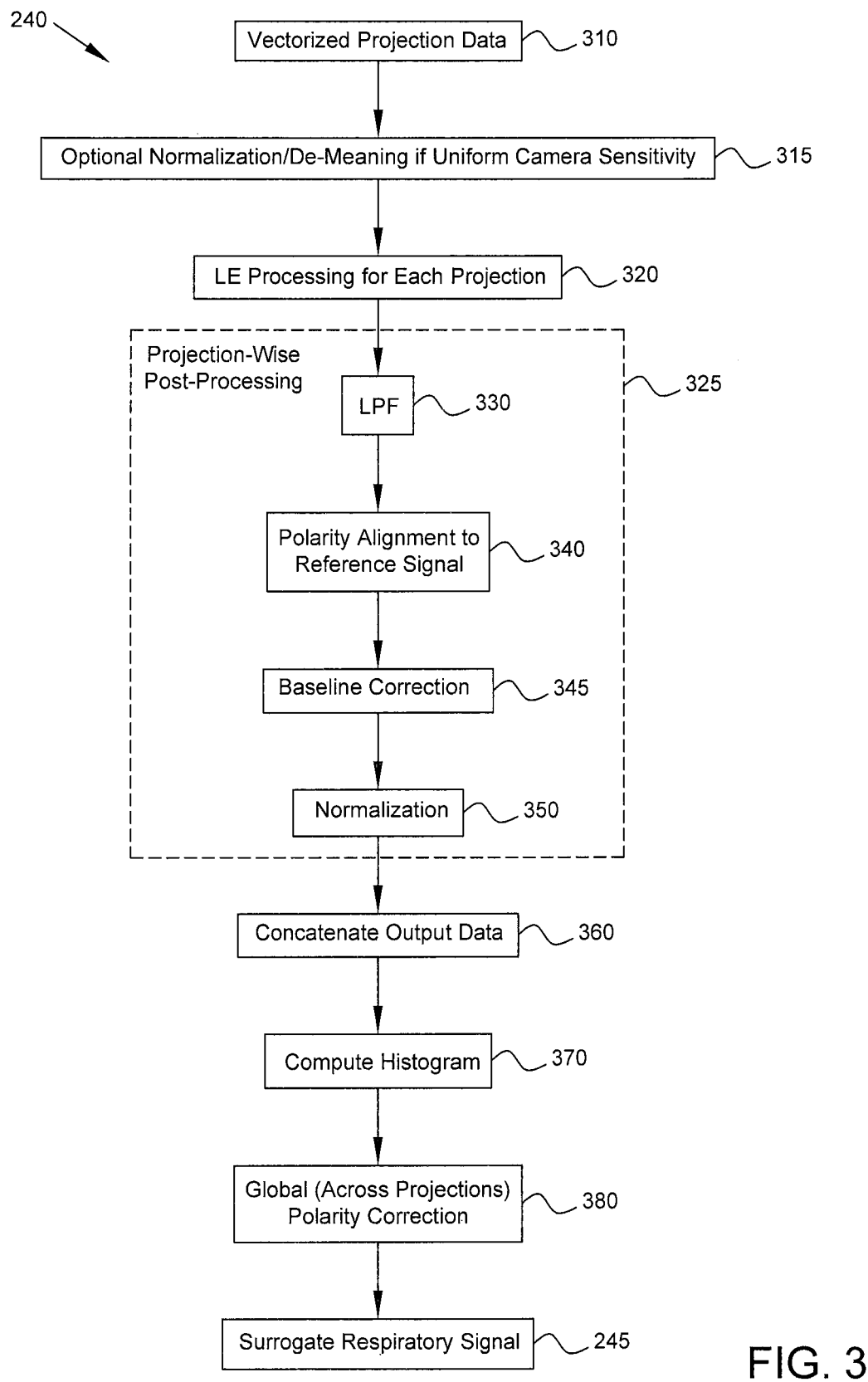
FIG. 3 is a flow diagram of the process of generating a surrogate respiratory signal in accordance with some embodiments.

FIG. 3 is a flow diagram that provides more detail regarding the process of generating a surrogate respiratory signal (block 240). LE processing (block 320) based on vectorized projection data 310 is performed on a per-projection basis, i.e., using the projection data from an individual projection. In some embodiments, if the camera sensitivity is uniform across the field of view (e.g., if a parallel-hole collimator is used), the input points x are normalized (e.g., by their standard deviation) and baseline-corrected (i.e., some quantity based on the statistics of each projection's surrogate is subtracted). Such processing (block 315) is performed so that when there is uniform camera sensitivity and motion confined to the field of view, bins with more photon counts than others will not have disproportionate influence. If, instead, an astigmatic collimator is used, such normalization and de-meaning (block 315) are not performed, because spatially varying sensitivity results in counts that are a function of the motion itself and thus capable of contributing to the surrogate signal estimate.

An adjacency matrix W is computed using the projection data of the individual projection, with each element of matrix W representing the distance, according to a predetermined distance metric, between high dimensional points $x_i$ and $x_j$ associated with time bins i and j, respectively. Matrix W can be interpreted as the connectivity matrix of a graph whose nodes are the input data points x in a relatively high-dimensional (M-dimensional) space. Each element $w_{i,j}$ is a weight factor that may be computed as follows:

$$w_{i,j} = \exp(-\|x_i - x_j\|_2^2 / \alpha) \quad (2)$$

where $\|\cdot\|_2$ denotes Euclidean distance (L-2 norm) and $\alpha$ (alpha) is an adaptive scale parameter or factor. The scale parameter $\alpha$ is a factor that is dependent on the projection data corresponding to the individual projection being used for the current LE processing. For a different projection, $\alpha$ will be re-computed. Details for computing $\alpha$ are provided below.

Traditional techniques for LE processing involve setting $\alpha$ to a constant that must be carefully tuned, with such a tuned constant value of $\alpha$ then being used for LE processing for all projections. In contrast, in embodiments of the present disclosure $\alpha$ is set adaptively based on the projection data corresponding to the particular projection for which LE processing is currently being performed. When computing matrix W according to equation (2), vectorized projection data corresponding to a single camera stop (i.e., single projection) are used. In some embodiments, the parameter $\alpha$ is set adaptively for that single projection as follows:

$$\alpha = \frac{1}{T^2} \sum_{i,j} \|x_i - x_j\|_2^2 \quad (3)$$

In other words, $\alpha$ is set to the mean squared Euclidean distance between input points $x_i$ and $x_j$ corresponding to a pair of time bins i and j, i.e., the average Euclidean distance between the high-dimensional input points for the current projection. This adaptive mechanism for setting $\alpha$ dispenses with the need to empirically determine a feasible constant value of $\alpha$ through laborious, and possibly inaccurate, tuning. Additionally, the use of an adaptive parameter $\alpha$ eliminates traditional concerns regarding possibly setting $\alpha$ too small, which causes all non-diagonal elements of W to go to zero, or too large, which causes all non-diagonal elements of W to go to unity. Both of the foregoing cases ($\alpha$ too small or too large) prevent LE processing from producing an accurate output, so that with traditional LE processing $\alpha$ must be chosen as a constant value in the transition region between those two asymptotes where $\alpha$ has a magnitude relevant to the values in W. The adaptive approach in accordance with embodiments of the present disclosure does not have the foregoing problem, as explained further below.

Figure 4:
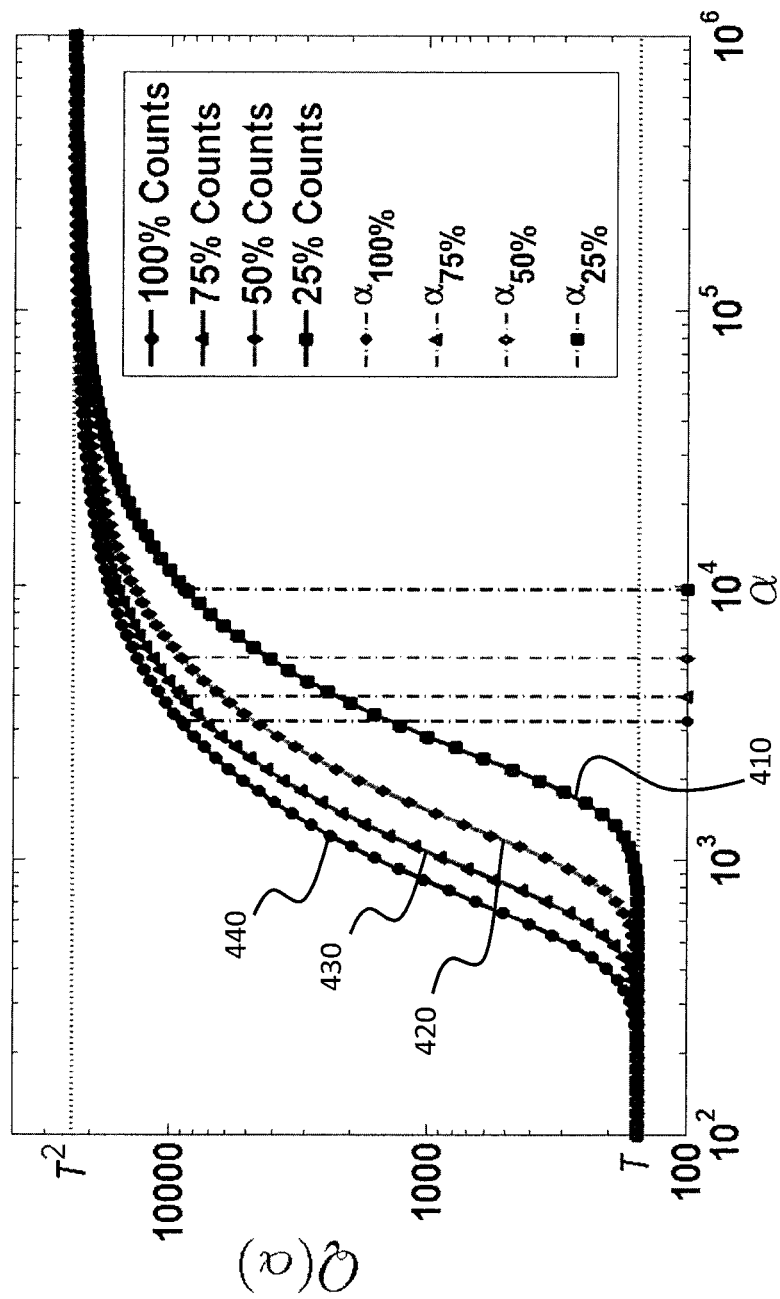
FIG. 4 is a plot that shows adaptive determination of the scale parameter $\alpha$ in accordance with some embodiments.

FIG. 4 is a plot that shows adaptive determination of the scale parameter $\alpha$ in accordance with some embodiments. In FIG. 4, the horizontal axis shows $\alpha$ plotted in log scale, and the vertical axis shows $Q(\alpha)$ plotted in log scale for example patient data, where $Q(\alpha)$ is defined as follows:

$$Q(\alpha) = \Sigma_{i,j} w_{i,j}(\alpha) \qquad (4)$$

Thus, $Q(\alpha)$ is the sum of all elements in the adjacency matrix W, as a function of the scale parameter $\alpha$. Each curve 410, 420, 430, 440 in FIG. 4 represents a different noise level generated via binomial subsampling of the counts in the original projection data. It can be seen that for all cases, the lower asymptote of $Q(\alpha)$ is T, the number of input points, and the upper asymptote is $T^2$. As image noise increases (indicated in the legend by reduced percentage of total counts), the transition region for a viable $\alpha$ (which must be between the lower and upper asymptotes) is shifted, partially explaining the difficulty in choosing a universal constant value for all acquisitions a priori as in traditional techniques for LE processing. However, as shown by the dashed vertical lines, setting the scale parameter $\alpha$ according to equation (3) provides good tracking of the transition region.

Thus, scale parameter $\alpha$ is determined dynamically for each projection, and $\alpha$ varies from projection to projection.

A matrix L referred to as a graph Laplacian is computed as follows based on W:

$$L = D - W \qquad (5)$$

where D, a diagonal matrix whose elements represent the degree of connectivity of each high-dimensional input point, is computed as follows:

$$D_{i,j} = \Sigma_j w_{i,j} \qquad (6)$$

Minimization of the objective function in equation (1) is equivalent to solving the following generalized eigenvalue problem:

$$L y_{n,*} = \lambda D y_{n,*} \qquad (7)$$

where $\lambda$ represents eigenvalues (for notational convenience, the index subscript of $\lambda$ is omitted) and $y_{n,*}$ is the eigenvector corresponding to the $n^{th}$ smallest nonzero eigenvalue and represents the $n^{th}$ row of matrix Y. In the following discussion, eigenvalues and eigenvectors refer to eigenvalues and eigenvectors according to equation (7). To obtain the N-dimensional output that will be the surrogate respiratory signal, the N eigenvectors corresponding to the N smallest nonzero eigenvalues are extracted.

In one embodiment, the single eigenvector corresponding to the smallest nonzero eigenvalue is computed, and the elements of that eigenvector are chosen as the amplitudes of the surrogate respiratory signal at respective times or time bins.

In another embodiment, corresponding to a scenario where there is a larger, transient motion that dominates the respiratory motion of the patient, the eigenvectors corresponding to the two smallest nonzero eigenvalues are computed, and the elements of the eigenvector corresponding to the second-smallest nonzero eigenvalue are chosen as the amplitudes of the surrogate respiratory signal. In this case, the eigenvector corresponding to the smallest nonzero eigenvalue may contain information regarding the larger, transient motion.

In general, any positive number of eigenvectors of the Laplacian matrix may be computed based on the adjacency matrix, and an N-dimensional surrogate respiratory signal is generated based on at least some of those generated eigenvector(s). The surrogate respiratory signal is indicative of respiratory activity by the patient, and this signal is usable for respiratory gating and gated image reconstruction to reduce or eliminate respiratory motion-induced blurring in images.

By solving the eigenvalue problem in equation (7), which in turn is based on the graph Laplacian matrix L defined in equation (5), embodiments of the present disclosure avoid the pruning of adjacency matrix W that is performed in traditional LE approaches. Traditionally, many elements of the adjacency matrix were set to zero to ensure that LE focuses on local structure in the data rather than global changes. Alternatively, traditional pruning was achieved by assigning the k nearest neighbors in the adjacency matrix to a bin. But, such pruning requires a priori decisions on how to threshold the elements of the adjacency matrix or the number of nearest neighbors to include in each bin. In contrast, by using equations (5) and (7) with adaptive scale parameter $\alpha$, elements of the adjacency matrix W fade to zero automatically in embodiments of the present disclosure, eliminating the need for such a priori decisions regarding pruning parameters. Consequently, reliable results are more readily available than with traditional pruning-based approaches, where good results were only possible after tedious tuning of parameters.

Thus, Laplacian eigenmaps, or configurations of output points generated from eigenvectors of the graph Laplacian, are used to reduce dimensionality of high dimensional input points that contain subtle variations based on respiratory motion that are difficult to exploit in the high dimensional space. The dimensionality reduction is achieved with an adaptive scale parameter $\alpha$ that provides good performance for SPECT.

In some embodiments, acquired projection data from each of P camera stops are disjoint in time and view angle and therefore are treated as a series of P independent measurements to obtain one matrix $Y_p$ with N rows and T columns for each camera stop p in $\{1, \ldots, P\}$. Thus, $Y_p = [y_1, \ldots, y_T]$ corresponds to the surrogate estimated at a single camera position, with each column representing the N-dimensional (N<<M) surrogate respiratory signal at a given time bin. In the case of a 1D surrogate signal (N=1), $Y_p$ reduces from a matrix to a vector $y_p$. Referring back to FIG. 3, after LE processing is performed for each projection individually (block 320), projection-wise post-processing 325, including blocks 330, 340, 345, and 350, is performed for each such matrix $Y_p$ (for each p in $\{1, \ldots, P\}$). For convenience, post-processing 325 is described below with respect to the special case of a 1D surrogate signal $y_p$, although in general similar post-processing may be performed for a surrogate signal of any dimensionality.

At block 330, a low-pass filter (LPF) may be used to smooth the output signal from the LE processing. For example, a Savitzky-Golay smoothing filter with a window size of nine and polynomial order of three may be used, because such an LPF preserves the magnitude of peaks in a noisy signal. Alternatively, other LPFs may be used in other embodiments.

Each vector $y_p$ (surrogate respiratory signal for projection p) is the output of an eigenvalue decomposition and thus is scaled by an arbitrary value, which could be positive or negative. Therefore, each $y_p$ must be polarity-corrected and normalized so that it is consistent in sign (polarity) and magnitude with others (i.e., for other projections) across the entire acquisition. To attain consistent polarity, a polarity alignment 340 is performed using a physical reference signal as an anchor throughout the acquisition. For example, a physical reference signal such as count rate over time may be used for acquisitions with spatially varying camera sensitivity (e.g., astigmatic collimation), and a physical reference signal such as the axial component of the image centroid (or some other centroid-based feature) may be used for parallel-hole collimation. Each $y_p$ is compared against the reference signal, e.g., by means of Pearson's correlation, and the polarity is reversed (i.e., the sign of each element in $y_p$ is flipped) if the correlation is negative (or positive, depending on a sign convention).

After projection-wise polarity correction 340, each $y_p$ is processed further (block 350) to address the effect that the above-described scaling by an arbitrary value has on magnitude. In some embodiments, a predetermined subset of the signal (e.g., lowest 10%) is extracted, e.g., $Y_{10\%} = \{y_t | y_t \leq 0.1 * \max(y_p) \text{ for all } t \text{ in } \{1, \ldots, T\}\}$. The entire $y_p$ is then baseline-corrected (block 345), e.g., by subtracting the mean of all elements of the subset, to yield $y_p'$ which may be called a baseline corrected signal. Signal $y_p'$ has a uniform baseline across all camera stops (i.e., for each projection p). To ensure a uniform magnitude as well, outliers (e.g., elements of $y_p'$ that are two or more standard deviations away from the mean) may be stripped from $y_p'$ to yield an outlier-free set $Y_{olf}$. Each $y_p'$ may then be normalized (block 350) by the standard deviation $\sigma_{olf}$ of the values in the outlier-free set $Y_{olf}$, e.g., by dividing each $y_p'$ by $(\sqrt{2} * \sigma_{olf})$, to yield a normalized signal $y_p''$ at projection p. Basing the baseline correction and normalization on statistics from percentiles and outlier-free portions of the data provides consistent performance even with noisy data, irregular breathing, and coughing. If the respiratory waveform is approximately sinusoidal, typical respiratory cycles will yield a peak-to-peak amplitude of two and a baseline of roughly zero for $y_p''$.

Figure 5:
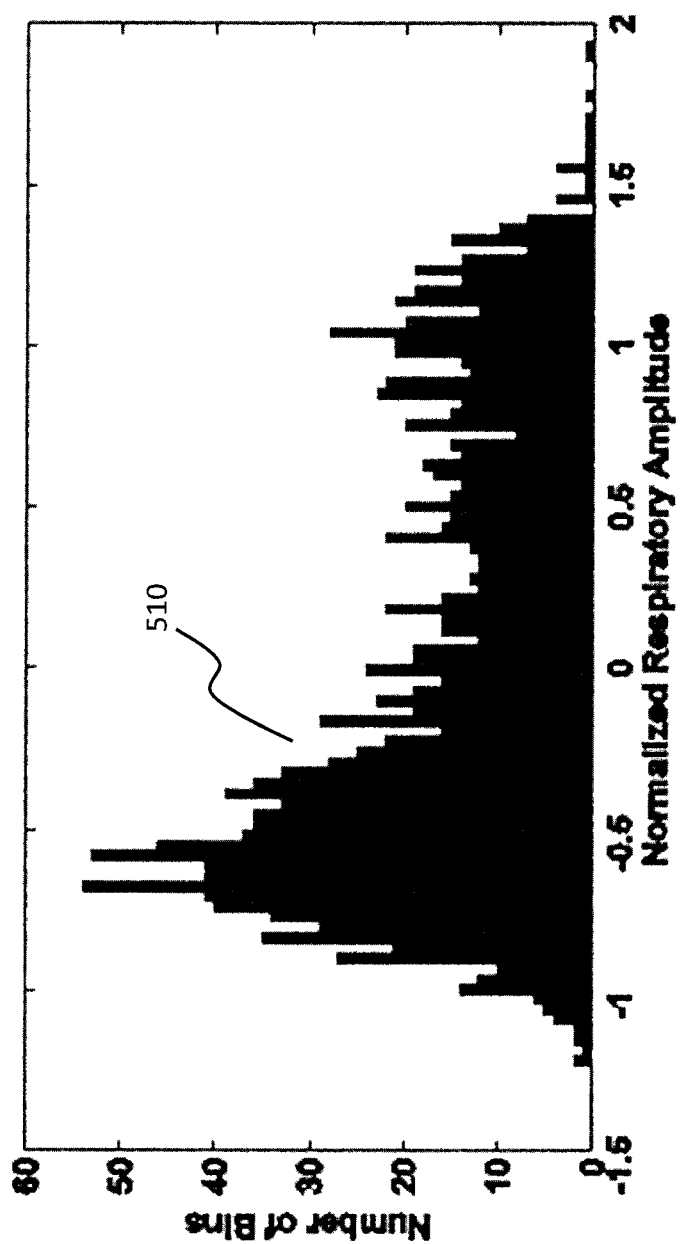
FIG. 5 is a histogram of an output surrogate respiratory signal in accordance with some embodiments.

Each $y_p''$ signal has consistent polarity and normalization relative to other signals for all p in $\{1, \ldots, P\}$ because of projection-wise polarity correction 340 and normalization 350, but there still may be a global (across all projections) polarity error. To correct this, all normalized $y_p''$ vectors corresponding to respective projections p are concatenated (block 360) to yield a vector $y_{out}$, which may be called an output signal or output vector. Output vector $y_{out}$ has dimensions PT×1, and in some embodiments vector $y_{out}$ is then inverted in polarity depending on the composition of the elements in $y_{out}$. In particular, because most time is spent in end expiration, it is known that histograms of respiratory amplitude tend to be bottom heavy (i.e., more occurrences of lower amplitudes rather than higher amplitudes). To enforce this constraint, a histogram of $y_{out}$ may be computed (block 370), and if the bottom-heavy property is not observed, the polarity of each element of $y_{out}$ is reversed by multiplying by −1 (block 380). An example bottom-heavy histogram 510 is shown in FIG. 5. In other embodiments, the opposite sign convention (invert if histogram is bottom heavy) may be used.

After global polarity correction 380, the resulting output vector $y_{out}$ represents a surrogate signal for respiratory amplitude (surrogate respiratory signal 245, see FIG. 2) throughout the entire acquisition as a function of time.

Figure 6:
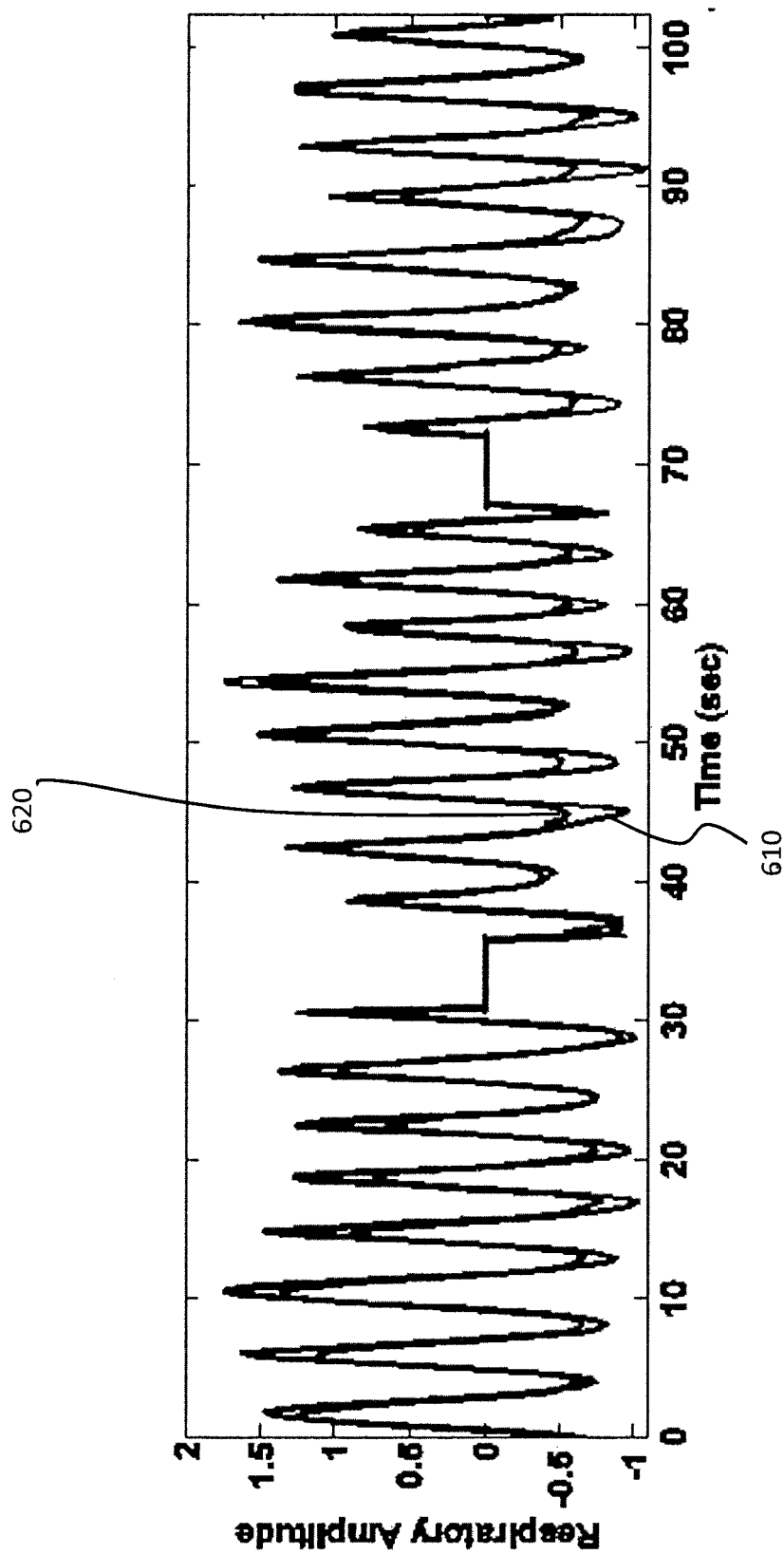
FIG. 6 is a plot of a surrogate respiratory signal in accordance with some embodiments.

FIG. 6 is a plot of a surrogate respiratory signal 610 in accordance with some embodiments. The time axis shown in FIG. 6 encompasses three projections from an acquisition corresponding to a patient at rest. Specifically, FIG. 6 encompasses a first projection corresponding to the interval from 0 to approximately 30 sec, a second projection corresponding to the interval from about 35 sec to about 65 sec, and a third projection corresponding to the interval from about 70 sec to about 100 sec. The flat regions in FIG. 6 represent rotation time between camera stops. A respiratory signal 620 obtained via an external sensor AZ-733V available from Anzai Medical Corp., Tokyo, Japan is also shown for reference. The external sensor AZ-733V includes an elastic belt and pressure sensor that measures the force exerted by the body surface because of respiration, and that external sensor is known to provide very accurate output. As seen in FIG. 6, surrogate respiratory signal 610 generated in accordance with embodiments of the present disclosure very closely matches the Anzai respiratory signal 620 and registers all respiratory peaks correctly. In FIG. 6 the success of the projection-wise and global post-processing operations is also evident. The three projection views are measured and processed independently from one another; nevertheless, the polarity is consistent and correct across the projections, and the scale of normalization is roughly uniform as well.

Thus, a flexible, accurate, improved approach for generating a surrogate respiratory signal to support gated reconstruction is presented in various embodiments. The processing of the projection data to generate the surrogate respiratory signal is fully automated (e.g., all processing in FIGS. 2 and 3 is performed automatically by computer processor 152).

Figure 7:
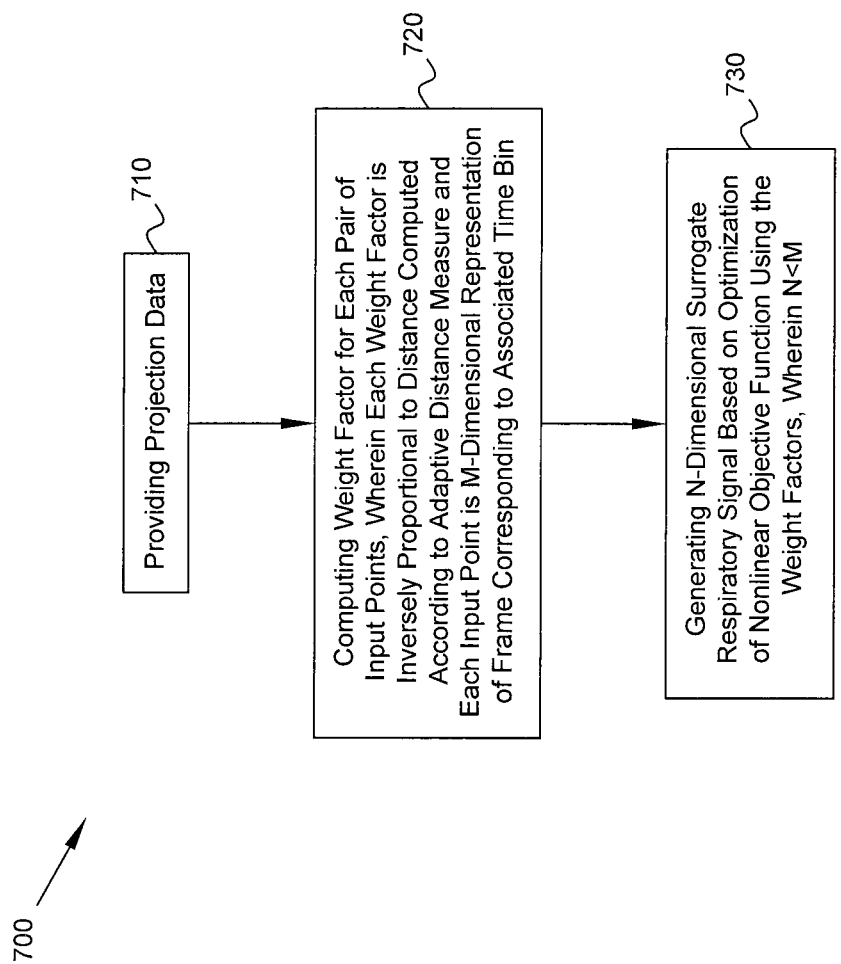
FIG. 7 is a flow diagram of a process in accordance with some embodiments.

FIG. 7 is a flow diagram of a process in accordance with some embodiments. Process 700 includes, at block 710, providing projection data acquired by one or more gamma detectors of a medical imaging system. The projection data represent detected counts of photons emitted by a radioisotope within a patient, where the counts are detected for a plurality of projections. The counts for each projection are binned into a plurality of time bins to provide respective frames of the projection data. At block 720, using a computer processor of the medical imaging system, a respective weight factor is computed for each pair of input points among a plurality of input points associated with respective time bins, each input point being an M-dimensional representation of the frame corresponding to the associated time bin for one of the projections, wherein each weight factor is inversely proportional to a distance computed between the corresponding pair of input points according to an adaptive distance measure that is dependent on the projection data corresponding to said one projection. Using the computer processor, an N-dimensional surrogate respiratory signal is generated (block 730) based on an optimization of a nonlinear objective function using the weight factors, wherein N<M and the surrogate respiratory signal is indicative of respiratory activity by the patient.

Figure 8:
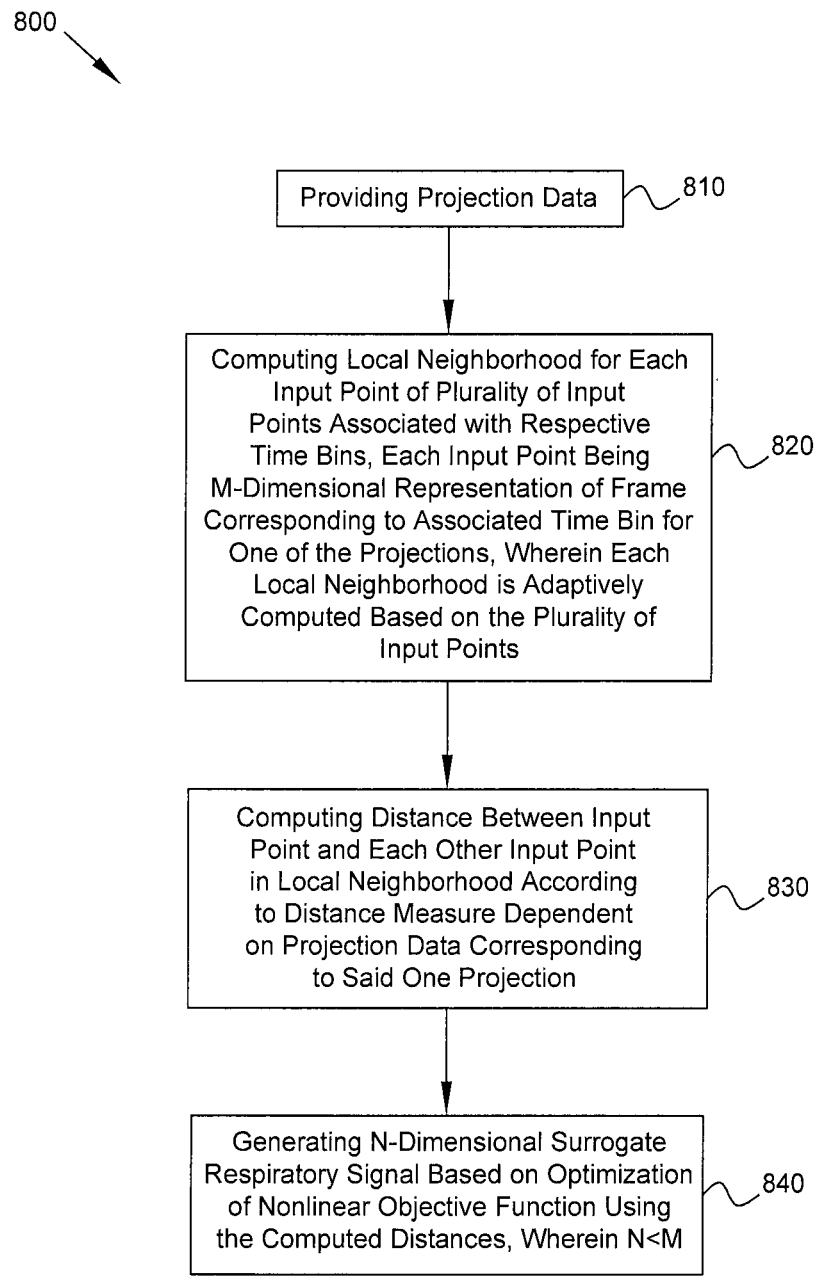
FIG. 8 is a flow diagram of a process in accordance with some embodiments.

FIG. 8 is a flow diagram of a process in accordance with some embodiments. Process 800 includes, at block 810, providing projection data acquired by one or more gamma detectors of a medical imaging system. The projection data represent detected counts of photons emitted by a radioisotope within a patient, where the counts are detected for a plurality of projections. The counts for each projection are binned into a plurality of time bins to provide respective frames of the projection data. At block 820, using a computer processor of the medical imaging system, a local neighborhood is computed for each input point of a plurality of input points associated with respective time bins, each input point being an M-dimensional representation of the frame corresponding to the associated time bin for one of the projections, wherein each local neighborhood is adaptively computed based on the plurality of input points. At block 830, using said computer processor, within the local neighborhood of at least one of the input points, a distance is computed between said at least one input point and each other input point in the local neighborhood according to a distance measure that is dependent on the projection data corresponding to said one projection. Using the computer processor, an N-dimensional surrogate respiratory signal is generated (block 840) based on an optimization of a nonlinear objective function using the computed distances, wherein N<M and the surrogate respiratory signal is indicative of respiratory activity by the patient.

Figure 9:
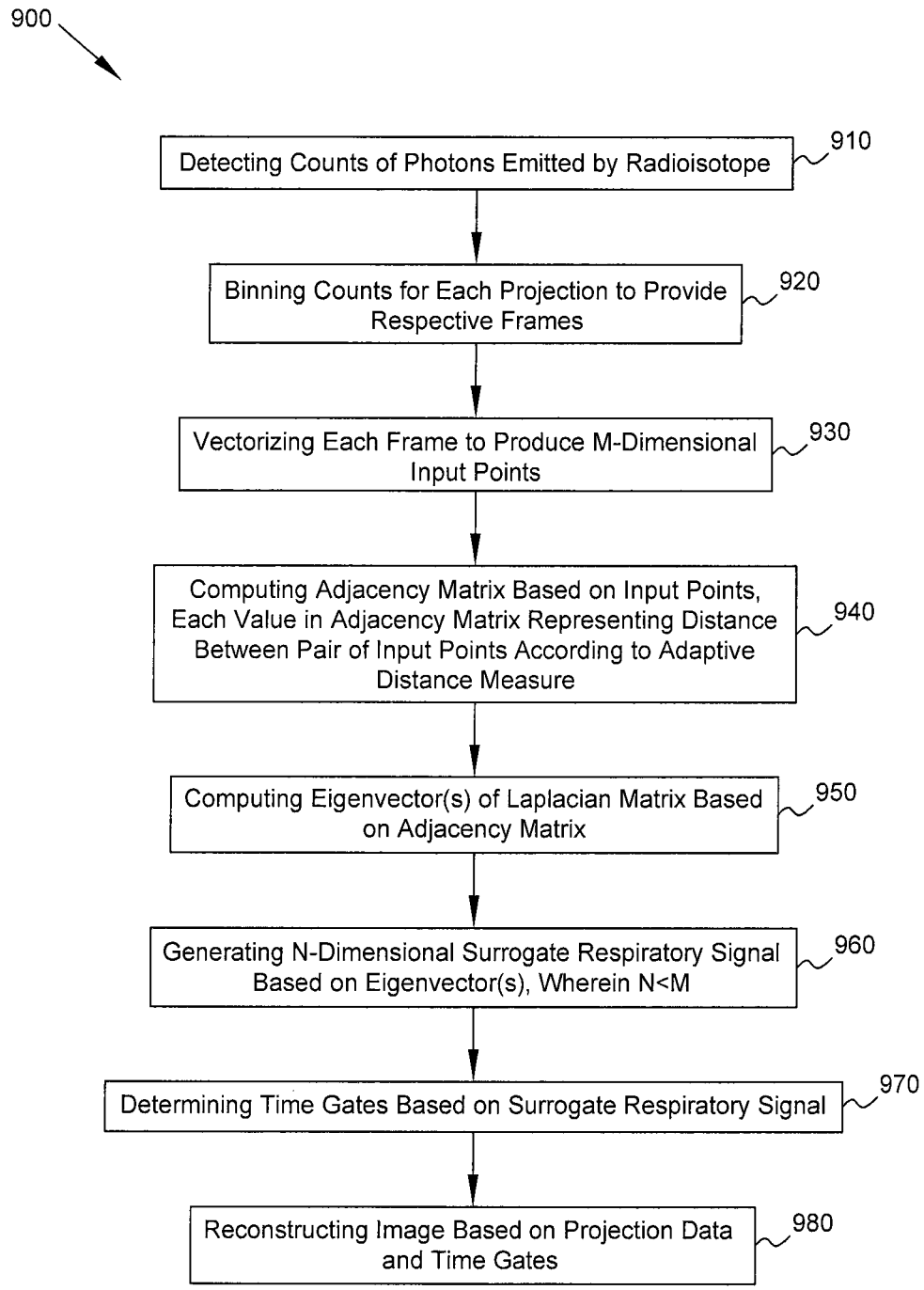
FIG. 9 is a flow diagram of a process in accordance with some embodiments.

FIG. 9 is a flow diagram of a process in accordance with some embodiments. Process 900 includes detecting (block 910), at one or more gamma detectors of a medical imaging system, counts of photons emitted by a radioisotope within a patient. The counts are detected for a plurality of projections corresponding to respective orientations of the one or more gamma detectors relative to the patient. At block 920, the counts for each projection are binned into a plurality of time bins to provide respective frames of the projection data. At block 930, using a computer processor of the medical imaging system, each frame for one of the projections is vectorized to produce a plurality of input points. Each input point is an M-dimensional vector representation of the corresponding frame. At block 940, using said computer processor, an adjacency matrix is computed based on the plurality of input points. Each value in the adjacency matrix represents a distance between a pair of said input points according to an adaptive distance measure based on a factor dependent on said one projection. At block 950, using said computer processor, one or more eigenvectors of a Laplacian matrix are computed based on the adjacency matrix. At block 960, using said computer processor, an N-dimensional surrogate respiratory signal is generated based on the one or more eigenvectors, wherein the surrogate respiratory signal is indicative of respiratory activity by the patient and N<M. At block 970, using said computer processor, a plurality of time gates are determined based on the surrogate respiratory signal. At block 980, using said computer processor, an image of a portion of the body of the patient is reconstructed based on the projection data and the plurality of time gates.

As discussed above, one advantage of the Laplacian eigenmaps (LE) approach for dimensionality reduction over PCA is its nonlinearity. LE can learn an arbitrary mapping from the high- to low-dimensional space that is not constrained by the linearity assumption of PCA. Another advantage of LE is the fact that it computes the mapping for each high-dimensional input point by considering the distances between it and other points within its local neighborhood. The locality attribute makes the LE approach more robust to noise and outliers than PCA, where the mapping is computed by analyzing the data's covariance matrix, which allows all points in the input data to affect the mapping for one point.

The concept of locality discussed herein is different than the term "local method" often used in the literature. Here, "Local method" refers to a DR technique with an objective function that seeks to preserve local structure in the data. Even so-called "global methods" that try to map global structures to the low-dimensional space may utilize local neighborhoods to describe the nature of that structure. In other words, the aspect of locality in various embodiments of the present disclosure refers to the way in which the DR technique informs itself about the structure of the high-dimensional input data, rather than the goals of that technique's objective function.

In general, locality is typically incorporated into DR methods in two ways: neighborhoods and weighting. To define a local neighborhood about an input point x, a distance function is needed to determine how far points are from the point of interest. The most commonly used distance function is the Euclidean distance, also known as the L-2 norm. Once a distance has been calculated between the point of interest and all others in the dataset, the neighborhood can be defined either by taking the k-nearest neighbors (i.e. the k points with the shortest distance to x), or by selecting only points with distances to x less than a predetermined threshold ε. Weighting is related to neighborhoods in that a distance measure usually appears in the equation for the weights. The most popular way of introducing weights is by means of a kernel. The most popular of these is variously referred to as the heat kernel or Gaussian kernel: $\text{kern}(x,z) = \exp(-\|x-z\|_2^2/\alpha)$. The L-2 norm appears in the exponent, as well as the scale parameter $\alpha$. Points close to the point of interest will have high weights and be more important to the DR method's objective function. Traditional DR methods call for a thresholding or k-nearest neighbor rule to be applied to the weights to further enforce locality.

The LE technique in some embodiments utilizes the heat kernel for weighting, sets $\alpha$ adaptively, and does not perform explicit pruning using k or ε. Because of the characteristics of the input data, $\text{kern}(x,z)$ will be zero (or very near zero) for many possible pairs of input points. This automatically prunes the adjacency matrix and obviates the need for explicit pruning by means of a threshold ε or k-nearest neighbor approach.

The concepts of locality and adaptive parameter selection can also be applied to nonlinear DR methods other than LE. As one example, the technique of diffusion maps is related to LE and also relies on the creation of an adjacency matrix. Although this matrix is normalized and handled differently than by LE, the distances between points are evaluated using the same exponential kernel, and the parameter $\alpha$ can be set adaptively in the same way (see equation (3)).

As another example of a nonlinear, local DR technique that may be used, an isomap seeks to minimize the objective function $\varphi(Y) = \Sigma_{i,j}(d_G(x_i,x_j) - d_G(y_i,y_j))^2$, where $d_G(\bullet,\bullet)$ is the geodesic distance between two points $x_i$ and $x_j$. The geodesic distance is, in turn, based on the Euclidean distances between points in a local neighborhood. The traditional implementation calls for a fixed k or threshold ε to determine what constitutes a neighborhood. Instead, analogous to the method for adaptively setting $\alpha$, the threshold ε may be set adaptively to the average of all Euclidean distance between points like in equation (3).

Another example of a nonlinear, local DR technique that may be used is Local Linear Embedding (LLE). LLE takes advantage of the fact that if a point $x_i$ is approximated by a linear combination of its neighbors as $x_i \approx \Sigma_{j \in N} c_j x_j$ for each point $x_j$ in the local neighborhood N about $x_i$, then the coefficients $c_j$ of the linear combination will be the same in the low-dimensional space. Thus, in a first step, the coefficients are fitted for each point, and in a second step, the low-dimensional representation is found using these coefficients. Just as with an isomap, the neighborhood for LLE may be defined using a threshold ε set to the average of all Euclidean distances between points.

In general, the method of using an adaptive parameter in the manner described in the examples above may be applied to any DR method that utilizes neighborhoods or weighting to examine the local structure of the input data.

The apparatuses and processes are not limited to the specific embodiments described herein. In addition, components of each apparatus and each process can be practiced independently and separately from other components and processes described herein.

The previous description of embodiments is provided to enable any person skilled in the art to practice the disclosure. The various modifications to these embodiments will be readily apparent to those skilled in the art, and the generic principles defined herein may be applied to other embodiments without the use of inventive faculty. The present disclosure is not intended to be limited to the embodiments shown herein, but is to be accorded the widest scope consistent with the principles and novel features disclosed herein.

What is claimed is:

1. A method of signal processing for medical imaging, the method comprising:
providing projection data acquired by one or more gamma detectors of a medical imaging system, the projection data representing detected counts of photons emitted by a radioisotope within a patient, the counts detected for a plurality of projections, the counts for each projection binned into a plurality of time bins to provide respective frames of the projection data;
using a computer processor of the medical imaging system, computing a weight factor for each pair of input points among a plurality of input points associated with respective time bins, each input point being an M-dimensional representation of the frame corresponding to the associated time bin for one of the projections, wherein each weight factor is inversely proportional to a distance computed between the corresponding pair of input points according to an adaptive distance measure dependent on the projection data corresponding to said one projection; and
using said computer processor, generating an N-dimensional surrogate respiratory signal based on an optimization of a nonlinear objective function using the weight factors, wherein N<M and the surrogate respiratory signal is indicative of respiratory activity by the patient.

2. The method of claim 1, wherein the weight factors are stored in an adjacency matrix, the method further comprising computing one or more eigenvectors of a Laplacian matrix based on the adjacency matrix;
wherein the N-dimensional surrogate respiratory signal is generated based on the one or more eigenvectors.

3. The method of claim 2, wherein the adaptive distance measure is further dependent on an average Euclidean distance between each pair of said input points.

4. The method of claim 3, wherein each value $w_{i,j}$ of the adjacency matrix is computed as: $w_{i,j}=\exp(-\|x_i-x_j\|_2^2/\alpha)$ for each pair of input points $x_i$ and $x_j$, wherein $\alpha$ is dependent on the average Euclidean distance between each pair of said input points.

5. The method of claim 4, further comprising:
using said computer processor, computing the Laplacian matrix as: $L=D-W$, wherein L is the Laplacian matrix, W is the adjacency matrix, and D is a diagonal matrix with each diagonal entry $D_{i,i}$ computed as: $D_{i,i}=\Sigma_j w_{i,j}$.

6. The method of claim 2, further comprising:
if the medical imaging system includes a parallel hole collimator, normalizing the plurality of input points by a standard deviation of the input points and normalizing the plurality of input points prior to computing the adjacency matrix.

7. The method of claim 2, wherein N=1, computing the one or more eigenvectors of the Laplacian matrix includes computing an eigenvector y corresponding to a smallest nonzero eigenvalue of the Laplacian matrix, and a value of the surrogate respiratory signal at each time bin i is equal to an element of said eigenvector y corresponding to said time bin i.

8. The method of claim 2, wherein computing the one or more eigenvectors of the Laplacian matrix includes computing an eigenvector y corresponding to a second-smallest nonzero eigenvalue of the Laplacian matrix, and a value of the surrogate respiratory signal at each time bin i is equal to an element of said eigenvector y corresponding to said time bin i.

9. The method of claim 2, further comprising:
for each projection p:
computing the adjacency matrix based on input points representing a frame of said projection p, computing the one or more eigenvectors of the Laplacian matrix, and generating the N-dimensional surrogate respiratory signal, to generate a surrogate respiratory signal corresponding to said projection p; and
reversing the polarity of at least one of the surrogate respiratory signals corresponding to a respective projection based on a correlation with a reference signal.

10. The method of claim 9, further comprising:
for each projection p:
baseline correcting a subset of the corresponding surrogate respiratory signal to generate a baseline corrected signal corresponding to said projection p; and
normalizing the baseline corrected signal based on a standard deviation of an outlier-free subset of values of the baseline corrected signal, to generate a normalized signal corresponding to said projection p.

11. The method of claim 10, further comprising:
concatenating the normalized signals corresponding to respective projections to generate an output signal;
generating a histogram of the values of the output signal; and
reversing the polarity of the output signal if the histogram satisfies a predetermined condition.

12. A non-transitory, machine-readable storage medium, tangibly embodying a program of instructions executable by a computer processor of a medical imaging system to cause the computer processor to perform operations comprising:
retrieving, from a memory of the medical imaging system, projection data acquired by one or more gamma detectors of the medical imaging system, the projection data representing detected counts of photons emitted by a radioisotope within a patient, the counts detected at a plurality of projections, the counts for each projection binned into a plurality of time bins to provide respective frames of the projection data;
computing a local neighborhood for each input of a plurality of input points associated with respective time bins, each input point being an M-dimensional vector representation of the frame corresponding to the associated time bin for one of the projections;
within the local neighborhood of at least one of the input points, computing a distance between said at least one input point and each other input point in the local neighborhood according to an adaptive distance measure, wherein the adaptive distance measure is dependent on the projection data corresponding to said one projection; and
generating an N-dimensional surrogate respiratory signal based on an optimization of a nonlinear objective function using the computed distances, wherein the surrogate respiratory signal is indicative of respiratory activity by the patient and N<M.

13. The non-transitory, machine-readable storage medium of claim 12, wherein the computed distances are stored in an adjacency matrix in the memory of the medical imaging system, each value in the adjacency matrix representing a distance between a pair of said input points according to the adaptive distance measure, and the instructions are executable by the computer processor to cause the computer processor to compute one or more eigenvectors of a Laplacian matrix based on the adjacency matrix;
wherein the N-dimensional surrogate respiratory signal is generated based on the one or more eigenvectors.

14. The non-transitory, machine-readable storage medium of claim 13, wherein the adaptive distance measure is further dependent on an average Euclidean distance between each pair of said input points.

15. The non-transitory, machine-readable storage medium of claim 13, wherein the instructions are executable by the computer processor to cause the computer processor to normalize the plurality of input points by a standard deviation of the input points and de-mean the plurality of input points prior to computing the adjacency matrix, if the medical imaging system includes a parallel hole collimator.

16. The non-transitory, machine-readable storage medium of claim 13, wherein N=1, computing the one or more eigenvectors of the Laplacian matrix includes computing an eigenvector y corresponding to a smallest nonzero eigenvalue of the Laplacian matrix, and a value of the surrogate respiratory signal at each time bin i is equal to an element of said eigenvector y corresponding to said time bin i.

17. The non-transitory, machine-readable storage medium of claim 13, wherein the instructions are executable by the computer processor to cause the computer processor to perform further operations including:
for each projection p:
computing the adjacency matrix based on input points representing a frame of said projection p, computing the one or more eigenvectors of the Laplacian matrix, and generating the N-dimensional surrogate respiratory signal, to generate a surrogate respiratory signal corresponding to said projection p; and
reversing the polarity of at least one of the surrogate respiratory signals corresponding to a respective projection based on a correlation with a reference signal.

18. The non-transitory, machine-readable storage medium of claim 17, wherein the instructions are executable by the computer processor to cause the computer processor to perform further operations including:
for each projection p:
baseline correcting a subset of the corresponding surrogate respiratory signal to generate a baseline corrected signal corresponding to said projection p; and
normalizing the baseline corrected signal based on a standard deviation of an outlier-free subset of values of the baseline corrected signal, to generate a normalized signal corresponding to said projection p.

19. The non-transitory, machine-readable storage medium of claim 18, wherein the instructions are executable by the computer processor to cause the computer processor to perform further operations including:
concatenating the normalized signals corresponding to respective projections to generate an output signal;
generating a histogram of the values of the output signal; and
reversing the polarity of the output signal if the histogram satisfies a predetermined condition.

20. A method of signal processing for medical imaging, the method comprising:
providing projection data acquired by one or more gamma detectors of a medical imaging system, the projection data representing detected counts of photons emitted by a radioisotope within a patient, the counts detected for a plurality of projections, the counts for each projection binned into a plurality of time bins to provide respective frames of the projection data;
using a computer processor of the medical imaging system, computing a local neighborhood for each input point of a plurality of input points associated with respective time bins, each input point being an M-dimensional representation of the frame corresponding to the associated time bin for one of the projections, wherein each local neighborhood is adaptively computed based on the plurality of input points;
using said computer processor, within the local neighborhood of at least one of the input points, computing a distance between said at least one input point and each other input point in the local neighborhood according to a distance measure dependent on the projection data corresponding to said one projection; and
using said computer processor, generating an N-dimensional surrogate respiratory signal based on an optimization of a nonlinear objective function using the computed distances, wherein N<M and the surrogate respiratory signal is indicative of respiratory activity by the patient.

* * * * *